United States Patent [19]

Ueno et al.

[11] Patent Number: 4,722,345
[45] Date of Patent: Feb. 2, 1988

[54] ULTRASONIC DIAGNOSTIC MULTIPLE-SECTOR IMAGE DISPLAY SYSTEM

[75] Inventors: Shinichirou Ueno; Hiroshi Fukukita, both of Tokyo; Koetsu Saito, Sagamihara; Tsutomu Yano, Kawasaki, all of Japan

[73] Assignee: Matsushita Electric Industrial Co., Ltd., Japan

[21] Appl. No.: 796,519

[22] Filed: Nov. 8, 1985

[30] Foreign Application Priority Data

| Nov. 9, 1984 | [JP] | Japan | 59-236133 |
| Dec. 19, 1984 | [JP] | Japan | 59-269076 |
| Dec. 20, 1984 | [JP] | Japan | 59-269760 |
| Dec. 26, 1984 | [JP] | Japan | 59-277902 |

[51] Int. Cl.⁴ .............................................. A61B 10/00
[52] U.S. Cl. ................................. 128/660; 358/112
[58] Field of Search .............. 338/89, 121; 318/663, 318/665, 668; 433/25; 358/112, 140; 367/7, 11; 343/55 D; 364/415, 515, 516; 73/620; 128/660-661

[56] References Cited

U.S. PATENT DOCUMENTS

| 4,002,827 | 1/1977 | Nevin et al. | 343/55 C |
| 4,106,021 | 8/1978 | Katagi | 343/55 C |
| 4,151,834 | 5/1979 | Soto et al. | 128/660 |
| 4,159,462 | 6/1979 | Rocha et al. | 367/97 |
| 4,167,753 | 9/1979 | Lynk | 358/140 |
| 4,207,507 | 6/1980 | Hermle | 318/663 X |
| 4,212,072 | 7/1980 | Huelsman et al. | 358/112 X |
| 4,224,829 | 9/1980 | Kawafuchi et al. | 73/626 |
| 4,245,250 | 1/1981 | Tiemann | 367/11 X |
| 4,271,706 | 6/1981 | Ledley | 73/614 |
| 4,287,768 | 9/1981 | Hayakawa et al. | 73/626 |
| 4,310,907 | 1/1982 | Tachita et al. | 128/660 X |
| 4,330,875 | 5/1982 | Tachita et al. | 367/105 |
| 4,348,902 | 9/1982 | Tachita et al. | 73/626 |
| 4,368,643 | 1/1983 | Tachita et al. | 73/626 |
| 4,423,737 | 1/1984 | Yano et al. | 128/661 |
| 4,440,025 | 4/1984 | Hayakawa et al. | 73/642 |
| 4,462,092 | 7/1984 | Kawafuchi et al. | 367/105 |
| 4,470,308 | 9/1984 | Hayakawa et al. | 73/642 |
| 4,471,449 | 9/1984 | Leavitt et al. | 358/112 X |
| 4,552,152 | 11/1985 | Tachita et al. | 128/663 |
| 4,567,897 | 2/1986 | Endo et al. | 128/660 |
| 4,582,065 | 4/1986 | Adams | 128/660 |
| 4,637,256 | 1/1987 | Sugiyama et al. | 73/633 |

FOREIGN PATENT DOCUMENTS

| 0066126 | 12/1982 | European Pat. Off. | 367/11 |
| 2310608 | 12/1976 | France | 128/660 |
| 2003355 | 3/1979 | United Kingdom | 358/140 |

OTHER PUBLICATIONS

Wells, P. N. T. "Biomedical Ultrasonics" 1977 Academic Press, pp. 306–307.
Ophir, J. et al, "Digital Scan Converters in Diagnostic UTS Imaging", Proc. IEEE, vol. 67, No. 4, Apr. 1979.
Thurstone, F. L. et al, "Actual Time Scan Conversion and Image Processing in a Phased Array Ultrasound Imaging System", 1977 IEEE Symp. Proc., Cat. #77CH1264-ISU Phoenix, Ariz. 28/28 Oct. 1977, pp. 247–249.
(Author Unk.) "A Real-Time UTS Diagnostic System for Simult Image Displays", JEEV. 16 #154 10/1979, pp. 66–69.
Bailey's Textbook of Anatomy, 18th Ed., ©1984 Williams & Wilkins Co., Baltimore, pp. 513–514.
Wells, P. N. T. "Ultrasonics in Clinical Diagnosis", Churchill Livingstone, N.Y. 1977, pp. 5, 158–159.

*Primary Examiner*—William E. Kamm
*Assistant Examiner*—Francis J. Jaworski
*Attorney, Agent, or Firm*—Lowe, Price, LeBlanc, Becker & Shur

[57] ABSTRACT

In an ultrasonic imaging system echo signals representative of the amplitude of ultrasonic energy returning along a plurality of angularly spaced paths are sampled at a constant speed and stored into a buffer memory. At a speed inversely proportional to the cosine of the angle of said path with respect to a reference line the echo samples are read out of the buffer memory and written into a specified area of a graphic memory at a constant speed in the direction of the rows thereof and at a speed proportional to the tangent of the angle of the path with respect to the reference line in the direction of the columns thereof. At a constant speed echo samples are read out of the graphic memory in the directions of the rows and columns and applied to a monitor to be displayed in a raster scan field.

9 Claims, 22 Drawing Figures

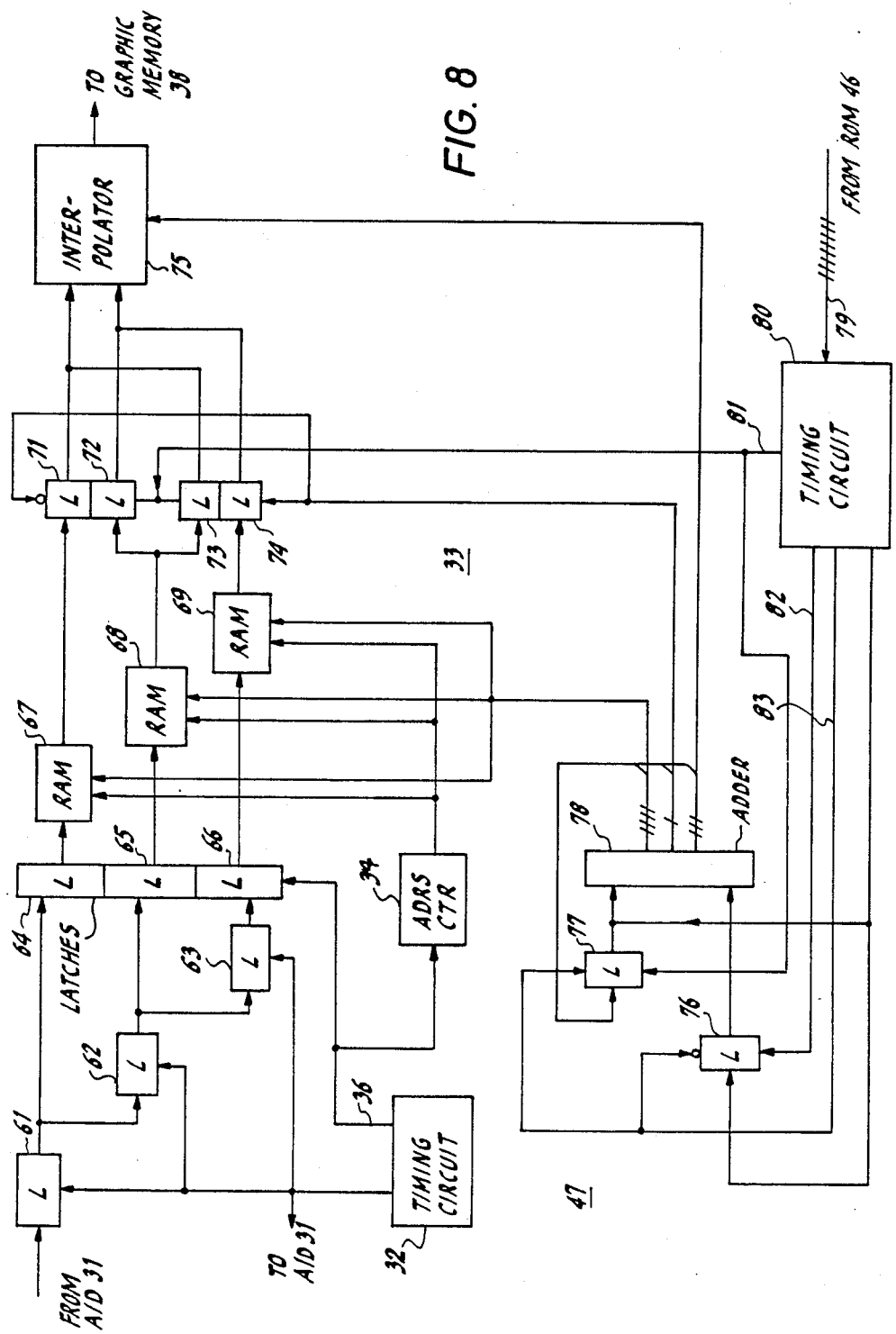

| SAMPLING ADDRESS | | | | | | | | | | INT'PL ADDRESS | | | SAMPLE POINTS | INT'PL POINTS |
|---|---|---|---|---|---|---|---|---|---|---|---|---|---|---|
| $Z_s'$ | 0 | 0 | 0 | 1 | 0 | 0 | 0 | 0 | 0 | 0 | 1 | 0 | 8, 9 | 8.250 |
| $\Delta Z'$ | 0 | 1 | 0 | 0 | 0 | 0 | 0 | 0 | 1 | 1 | 0 | 0 | — | 1.125 |
| $Z_s' + \Delta Z'$ | 0 | 0 | 0 | 0 | 0 | 1 | 1 | 1 | 1 | 1 | 1 | 0 | 9, 10 | 9.375 |
| $Z_s' + 2\Delta Z'$ | 0 | 0 | 0 | 1 | 1 | 0 | 1 | 0 | 0 | 0 | 0 | 1 | 10, 11 | 10.500 |
| $Z_s' + 3\Delta Z'$ | 0 | 0 | 0 | 1 | 1 | 1 | 0 | 1 | 1 | 1 | 0 | 1 | 11, 12 | 11.625 |
| $Z_s' + 4\Delta Z'$ | 0 | 0 | 1 | 1 | 1 | 0 | 1 | 0 | 1 | 0 | 1 | 1 | 12, 13 | 12.750 |
| $Z_s' + 5\Delta Z'$ | 0 | 1 | 1 | 1 | 1 | 1 | 1 | 1 | 1 | 1 | 1 | 1 | 13, 14 | 13.875 |
| $Z_s' + 6\Delta Z'$ | 0 | 1 | 0 | 1 | 1 | 1 | 1 | 0 | 0 | 0 | 0 | 0 | 15, 16 | 15.000 |
| $Z_s' + 7\Delta Z'$ | 1 | 0 | 0 | 0 | 0 | 1 | 0 | 0 | 1 | 1 | 0 | 0 | 16, 17 | 16.125 |
| $Z_s' + 8\Delta Z'$ | 1 | 0 | 0 | 0 | 0 | 0 | 0 | 0 | 1 | 0 | 1 | 0 | 17, 18 | 17.250 |
| ⋯ | ⋯ | ⋯ | ⋯ | ⋯ | ⋯ | ⋯ | ⋯ | ⋯ | ⋯ | ⋯ | ⋯ | ⋯ | ⋯ | ⋯ |

*FIG. 10*

ULTRASONIC DIAGNOSTIC MULTIPLE-SECTOR IMAGE DISPLAY SYSTEM

BACKGROUND OF THE INVENTION

The present invention relates to an ultrasonic imaging system. The invention is particularly suitable for dental diagnostic applications, particularly for analyzing the surrounding structures of teeth for diagnosing periodontitis.

For dental diagnostic application, a toothbrush-like ultrasound probe is used. A piezoelectric transducer is swung in a pendulum motion to emit an acoustic beam in a sector field. The acoustic beam is transmitted in the form of a burst pulse to a tooth to be examined. The probe is connected to an ultrasonic imaging system for converting echoes returning along a plurality of angularly spaced paths into electrical echo signals. For providing the echo signals on display, the sector scan format is converted to a conventional raster scan format. It is convenient for dentists to be able to display a number of dental tomographic images on separate areas of a monitor screen. However, the need to employ typical prior art scan conversion techniques would result in an ultrasonic multiple imaging system which is complex and costly.

SUMMARY OF THE INVENTION

It is therefore an object of the present invention to provide a low-cost ultrasonic imaging system which allows display of sector-scanned multiple ultrasound images on a single monitor screen.

According to a broader aspect, the ultrasonic imaging system of the invention provides visual display of successively received echo signals representative of the amplitude of ultrasonic energy returning along a plurality of angularly spaced paths in a sector scan field with a successive angular increment with respect to a reference line. The echo signals are sampled at constant time intervals and supplied to a buffer so that echo samples align on concentric semicircles on a sector scan field. A main memory having cells arranged in a matrix of rows and columns is provided. An area defining circuit is provided to define a plurality of storage areas within the main memory. A write address circuit for the main memory is provided for addressing cells of one of the defined storage areas so that the successively addressed cells are spaced apart in the direction of columns by intervals variables as a function of the angle of deflection of each of the transmission paths with respect to a fixed reference line and spaced apart in the direction of the rows by constant intervals. The echo samples are rewritten from the buffer into the addressed cells. In this way, a plurality of sector scan images can be stored respectively in the defined areas of the main memory. The main memory is then addressed at constant rates in the column and row directions in a television scan format to read the stored data onto a raster scan field of a monitor screen. Preferably, a reconstructive interpolator is provided between the buffer memory and the main memory for deriving reconstructive interpolated echo samples from successive ones of echo samples read out of the buffer memory and applying the derived echo samples to the main memory. The interpolating echo samples are representative of virtual echo samples on each of the transmission paths which are spaced apart by intervals inversely proportional to the cosine of the angle of deflection of each transmission path so that they would appear to align on lateral lines perpendicular to the reference line on the sector scan field.

BRIEF DESCRIPTION OF THE DRAWINGS

The present invention will be described in further detail with reference to the accompanying drawings, in which:

FIG. 8 is a block diagram illustrating details of the buffer memory and adder of FIG. 3;

FIG. 10 is an illustration of sampling and interpolation address data useful for describing the operation of the circuit of FIG. 8;

DETAILED DESCRIPTION

Figure 1:
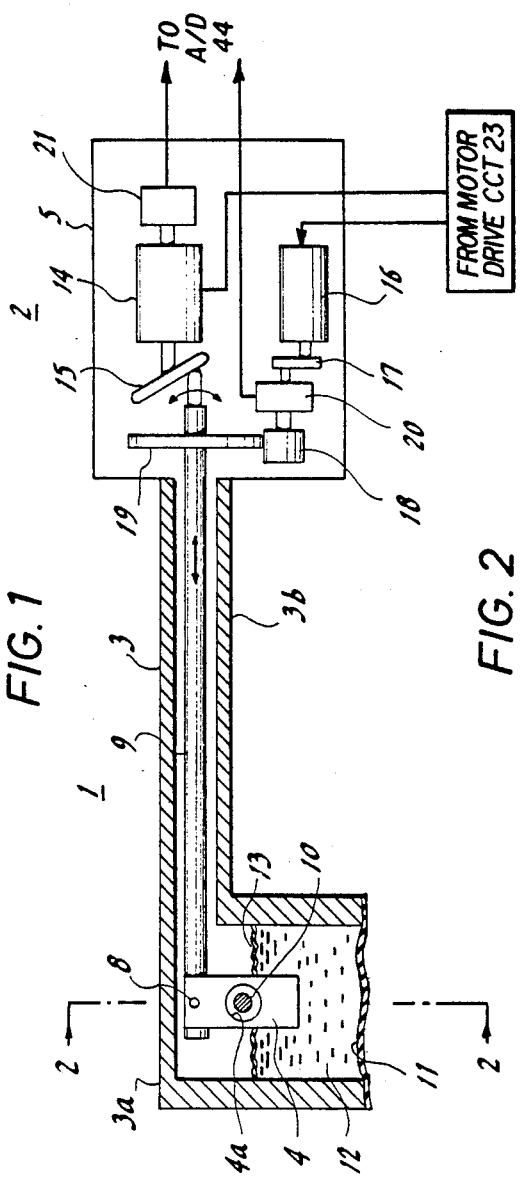
FIG. 1 is an illustration of a typical example of an ultrasonic dental dignostic probe.
Figure 2:
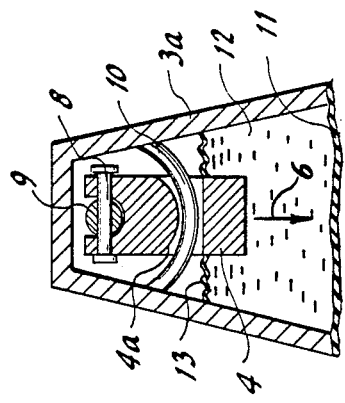
FIG. 2 is a cross-sectional view taken along the lines 2—2 of FIG. 1.

Before going into the detail of the present invention, it is appropriate to describe the structure and operation of an ultrasonic dental diagnostic probe 1 with reference to FIGS. 1 and 2. Probe 1 is generally in the shape of a toothbrush and comprises a hand grip portion 2 having a dual motion drive mechanism and an arm portion 3 having a downwardly flared, head portion 3a accommodating an ultrasonic single-element focusing transducer 4 and a hollow arm portion 3b connected between head portion 3a and hand grip portion 2. The arm portion 3b has a sufficient length to allow the head portion to reach the innermost part of the patient's teeth. Transducer 4 operates as a transmitter for emission of an acoustic beam of short-duration pulse burst during a transmit mode and operates as a sensor during a receive mode to convert returning echoes from into electrical echo signals.

Transducer 4 is rotatably mounted by a pin 8 on the free end of a drive shaft 9. An arcuate guide arm 10 extends from one inner side wall of the housing of head portion 3a through an opening 4a of transducer 4 to the other inner side wall so that transducer 4 is swingable about guide arm 10 in a first plane and is further swingable about the axis of drive shaft 9 in a second plane normal to the first plane. Head portion 3a has a lower open end sealed fluid-tightly with a flexible diaphragm 11 of a material which is transparent to acoustic energy.

Head portion 3a is partially filled with liquid 12 in which the energy radiating face of transducer 4 is submerged. Liquid 12 is of a material which allows acoustic energy to propagate with minimum loss and which provides an acoustic impedance match between the transducer and object. One suitable material for the liquid is water. Liquid 12 is contained by a sealing member 13 which provides fluid-tight sealing between the housing's inner walls and the side walls of transducer 4. To permit transducer 4 to swing in the orthogonal directions, sealing member 13 is flexible and preferably formed into a corrugated, bellows-like shape.

The dual motion drive comprises a first micromotor 14 with its rotor shaft firmly coupled to a swash-plate cam 15 having its cam face in camming contact with a proximal end of drive shaft 9. A second micromoter 16 drives an eccentric cam 17 which translates the rotary motion to a swing motion, the latter being transmitted by a friction wheel 18 to a friction wheel 19 which is fixedly mounted on drive shaft 9.

Drive shaft 9 therefore provides reciprocating motion and swing motion. Transducer 4 swings on a transverse plane about shaft 9 to transmit an acoustic burst pulse in a sector scan field along each of a plurality of angularly spaced paths to allow a series of echo pulses to return to transducer 4 before the next pulse burst is emitted. Transducer 4 further swings about guide 10 as shaft 9 is reciprocated to shift the sector scan field to the next in succession to obtain three-dimensional tomographic information.

An angular position sensor, or a potentiometer 20 is connected to the friction wheel 18 to generate a signal indicating the angular position of transducer 4 on the sector scan field and hence the angle of each echo returning path. A second angular position sensor 21 is connected to the motor 14 to generate a signal indicating the angle of the deflection of sector scan field with respect to a plane perpendicular to the shaft 9. Motors 14 and 16 are respectively controlled by a motor drive circuit 23 which is in turn controlled by a keyboard 51, FIG. 3. Motor 14 may be selectively driven by circuit 23 to cause transducer 4 to be deflected about shaft 10 on one side of a zero-angle position to a desired angle which angle may be successively changed to obtain a plurality of scans.

With the transducer 4 so deflected about shaft 10 and held stationary on that desired plane, the switch 22 is operated to couple the output of sensor 20 to A/D converter 44 and motor 16 is controlled to cause the transducer 4 to oscillate about shaft 9 to perform a sector scan on that deflected plane.

Apparatus for selection of a fixed scan angle and for scan servo control is per se well-known, see for example U.S. Pat. No. 4,151,834. Motor 14 is controlled to cause transducer 4 to oscillate about shaft 10 to perform a sector scan. Thus, a plurality of sector-scan images can be obtained in response to signals from keyboard 51 by successively changing the angle of deflection of the sector-scan plane with the aid of displayed angle data. In operation, the diaphragm 11 of the probe is held against the surrounding structure of a tooth, or gingiva.

Figure 3:
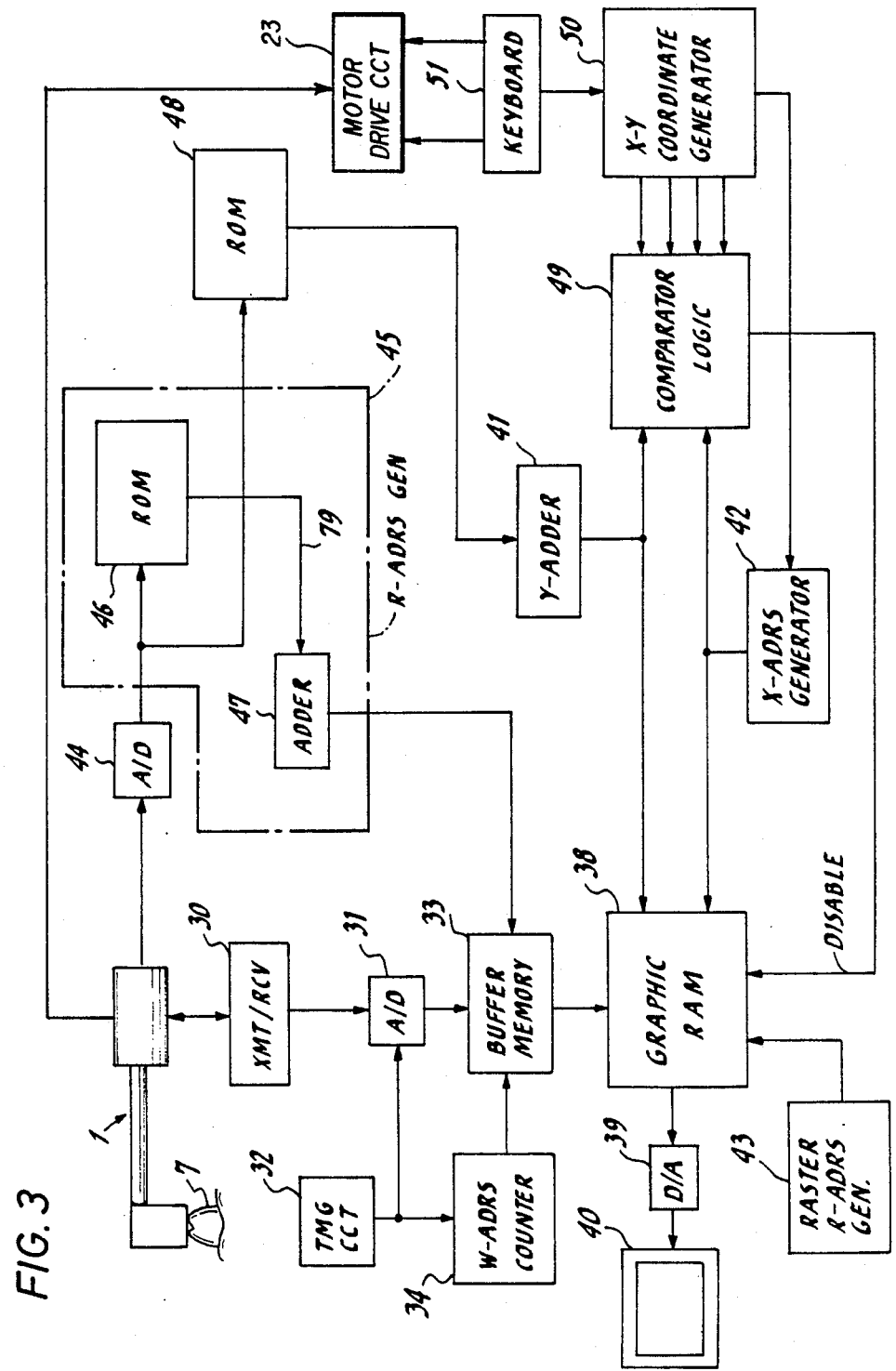
FIG. 3 is a block diagram of an ultrasonic imaging apparatus according to a preferred embodiment of the invention.

Referring now to FIG. 3, there is shown an ultrasonic dental diagnostic imaging system according to a preferred embodiment of the present invention. The system includes a transmit-receive unit 30 from which acoustic energy in the form of a pulse burst is supplied to the probe 1 and by which returning echoes are detected. The detected echoes are sampled at constant time intervals corresponding to $\Delta Z$ by an A/D converter 31 in response to clock pulses supplied from a timing circuit 32 and converted to echo amplitude data. A write-address counter 34 generates a writing addresss code by counting the clock pulse from timing circuit 32 to write the echo amplitude data at intervals $\Delta Z$ into a buffer memory 33, so that the sampled points on radial lines would appear as dots on concentric semicircles shown in FIG. 4.

A graphic RAM 38, or main memory of a matrix array, is connected to the output of buffer memory 33 and in turn supplies its output through a D/A converter 39 to a video monitor 40. Graphic memory 38 is addressed in response to a Y-address code generated by a Y-adder 41 at constant time intervals in synchronism with the readout of echo samples from buffer memory 33 and in response to an X-address code supplied from an X-address generator 42 simultaneously with the Y address code, so that all the buffered echo samples are written into the addressed cells of one of the specified storage areas of graphic memory 38. X-address generator 42 essentially comprises a presettable counter and a clock generator. The presettable counter is preset to an initial count value supplied from X-Y coordinate generator 50 each time the echo sample data are transferred from buffer memory 33 to graphic memory 38. The initial count value represents the starting column position Xs of each sector-scanned image to be stored into the graphic memory.

Graphic memory 38 is subsequently addressed by a raster-scan address generator 43 to read the stored data at constant time intervals in the directions of rows and columns to display the sector-field images in a raster scan format on the monitor 40.

Figure 4:
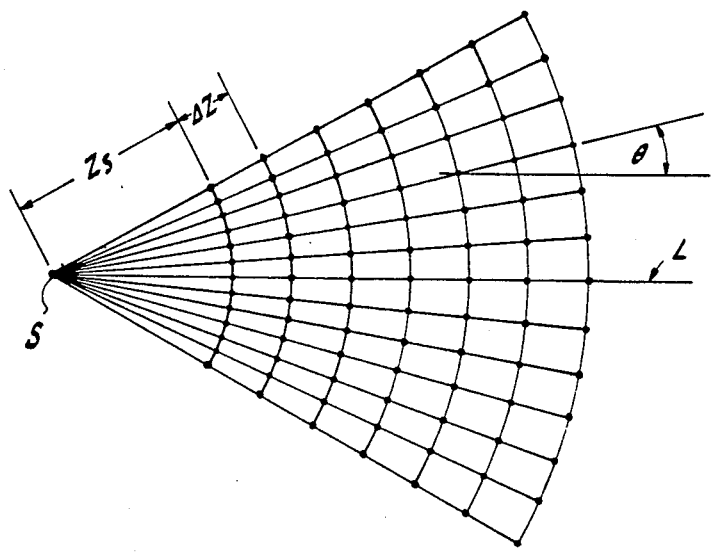
FIG. 4 is an illustration of echo signals sampled at points in a sector scan field.

The angular position signal from the probe 1 indicates the angle of each beam transmission path which increases at substantially equal angular increments with respect to a reference line L, FIG. 4. The angular position signal is digitized by an A/D converter 44 and fed to a read-address generator 45 which includes a read-only memory 46 storing scan-conversion data which is read in response to the digitized angular position data out of the memory into an adder 47 which to generate an address code for reading echo data from the buffer memory 33.

To transfer echo samples from buffer memory 33 to graphic memory 38, it is preferred to exclude insignificant echo samples which exist in the near-field of the sector scan. Echoes occurring in a period Zs, FIG. 4, along each angularly spaced path from a point source S to a point displaced a distance Zs from the source are considered to be insignificant and are therefore discarded when read out of the buffer memory 33.

Specifically, the scan conversion data in ROM 46 comprise a plurality of data sets each corresponding to each of the beam transmission paths, each data set including an initial value indicating the distance ZS and an incremental value indicating the interval $\Delta Z$. Each of the scan conversion data sets is read out of ROM 46 as the scanned beam is angulated with an equal angular increment and supplied to the adder 47. An incremental address code for reading buffer memory 33 is generated therefor by adder 47 by successively adding the incremental value $\Delta Z$ to the initial value Zs. The buffer reading address code can be represented by $Zs + i \cdot \Delta Zs$, where i is an integer ranging from zero to N, where N is the maximum number of echo samples to be read out of buffer 33 for each radial transmission path.

Figure 5:
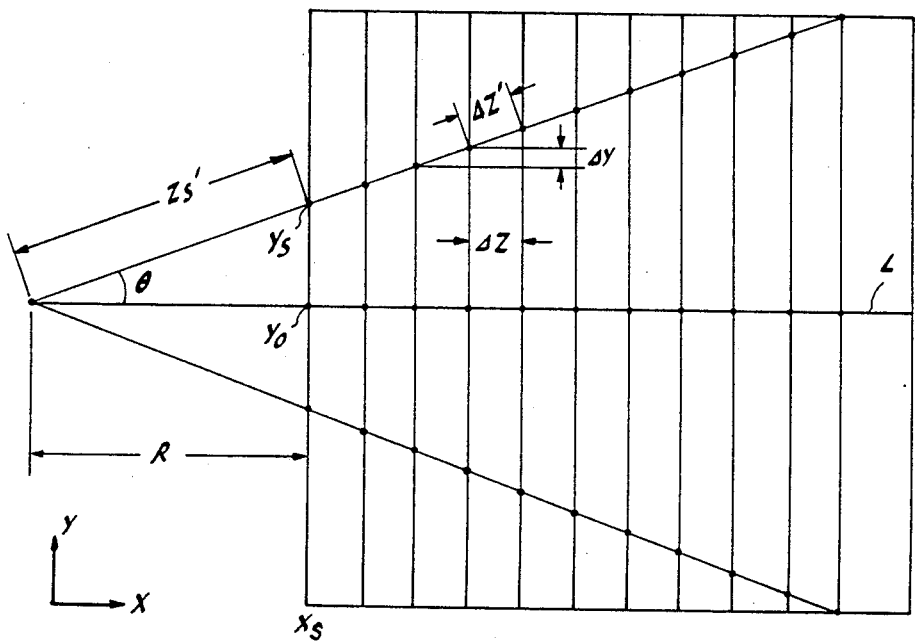
FIG. 5 is an illustration of the storage locations of echo samples in the graphic memory of FIG. 1.

Scan conversion data similar to those in ROM 46 are stored in a ROM 48 which are read in response to the angular position data from A/D converter 44 and fed to the Y-adder 41 simultaneously with the reading of scan conversion data out of ROM 46. The data stored in ROM 48 comprises a plurality of data sets each comprising an initial Y-address code and an incremental Y-address code. As shown in FIG. 5, the initial Y-address code is a variable Ys indicating the starting position of storage cells for a series of echo samples derived from each transmission path on the Y-axis of the X-Y coordinates of the main memory 38 and also indicating a displacement from a reference point Yo. The incremental Y-address code is a variable $\Delta Y$ indicating the interval between successive storage cells in the graphic memory 38 which are addressed during write modes in the direction of Y-coordinate, or columns. These variables are represented by:

$Ys = Yo + R \cdot \tan \theta$ (where R is a distance between a virtual point source S' and the starting address point Xs)

$\Delta Y = \tan \theta$

Y-adder 41 accumulatively adds the incremental value $\Delta Y$ to the initial value Ys in a manner identical to that performed by adder 47 to derive an incremental Y-address variable represented by $Ys + i \cdot \Delta Y$. X-address generator 42 produces X-address codes represented by $Xs + i \cdot \Delta X$ (where $\Delta X$ corresponds to $\Delta Z$) for writing echo samples read out of buffer memory 33 into graphic memory 38 in the direction of X-coordinates, or rows which are spaced apart by intervals $\Delta Z$. With the scan conversion data stored in both read-only memories 46 and 48, the echo samples stored in buffer memory 33 which align on concentric semicircles are realigned on lateral lines, or columns perpendicular to the reference line L, or X-coordinates in the main memory 38.

To store a plurality of sector-field images into the graphic memory 38, the outputs of Y-adder 41 and X-address generator 42 are connected to a comparator logic 49 which compares X- and Y-address data with X- and Y-coordinate data supplied from an X-Y coordinate generator 50 which may be implemented by a microprocessor. A keyboard 51 is connected to the X-Y coordinate generator to generate a set of X-Y coordinates which divide the whole area of the graphic memory 38 into separate display areas.

Figure 6:
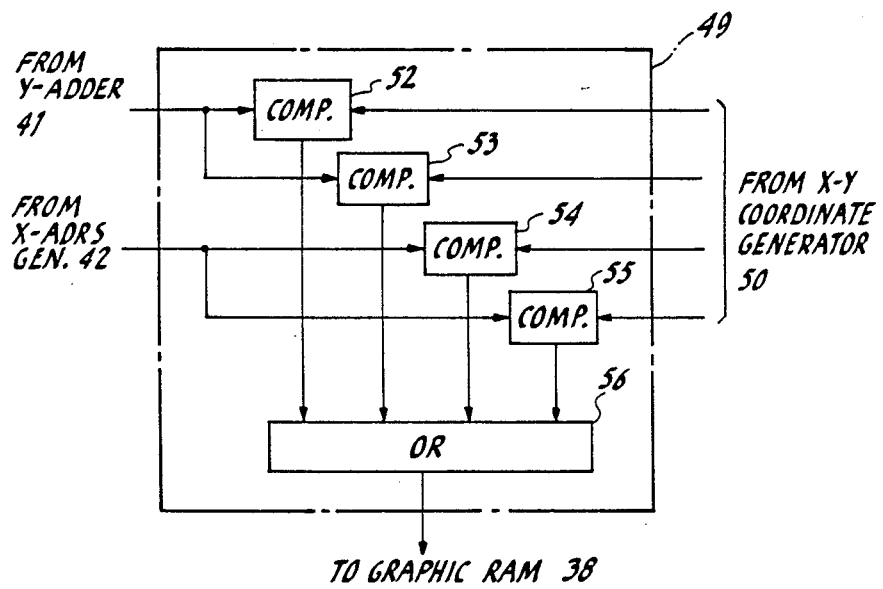
FIG. 6 is an illustration of details of the comparator logic of FIG. 3.

As shown in FIG. 6, the comparator logic 49 includes digital comparators 52-55 and an OR gate 56. Comparators 52 and 53 compare Y-address data from Y-adder 41 with Y-coordinates indicating upper and lower limits of the subdivision specified by data entered to the keyboard 51. Each of the comparators 52, 53 supplies a logical 0 to OR gate 56 when the Y-address data is within the range between the upper and lower limits and supplies a logical 1 to OR gate 56 when it is outside the limits. Likewise, comparators 54 and 55 compare X-address data from X-address generator 42 with X-coordinates indicating left- and right-side limits of the subdivision specified by the entered data. Each of the comparators 54, 55 supplies a logical 0 to OR gate 56 when the X-address data is within the range between the left- and right-side limits and supplies a logical 1 output when it is outside the left- and right-side limits. The output of OR gate 56 is applied to the graphic memory 38 to disable its read and write operations when the OR gate output is at logical 1. Thus, graphic memory 38 is enabled as long as the location specified by the X- and Y-address codes is within the subdivided area.

Figure 7A:
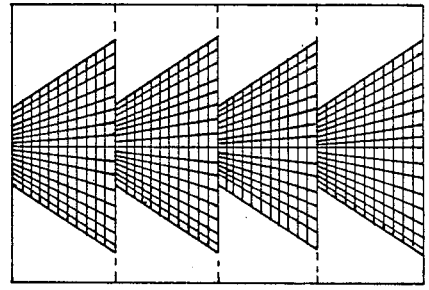
FIGS. 7A and 7B are illustrations of sector-scan fields displayed on separate areas of a monitor screen.
Figure 7B:
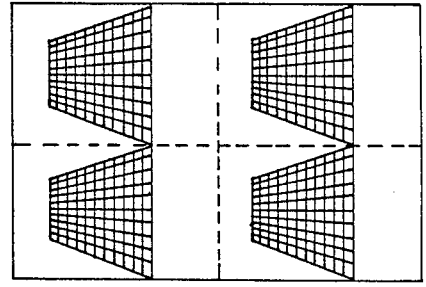

Keyboard 51 is manipulated in coaction with the probe so that when a sector-scan tomographic image is stored in the buffer memory 33, keyboard 51 specifies a particular area of the screen of monitor 40 as mentioned above to transfer the image from buffer memory 33 to the specified area of the graphic memory 38. With a given image being loaded into graphic memory 38, the probe 1 is moved to the next position to store the next image into buffer memory 33, followed by the operation of keyboard 51 to specify the next area on the monitor screen and transfer the image to graphic memory 38. FIG. 7A and 7B are typical examples of plural sector-scan tomographic images on separate areas of the monitor screen.

Figure 9:
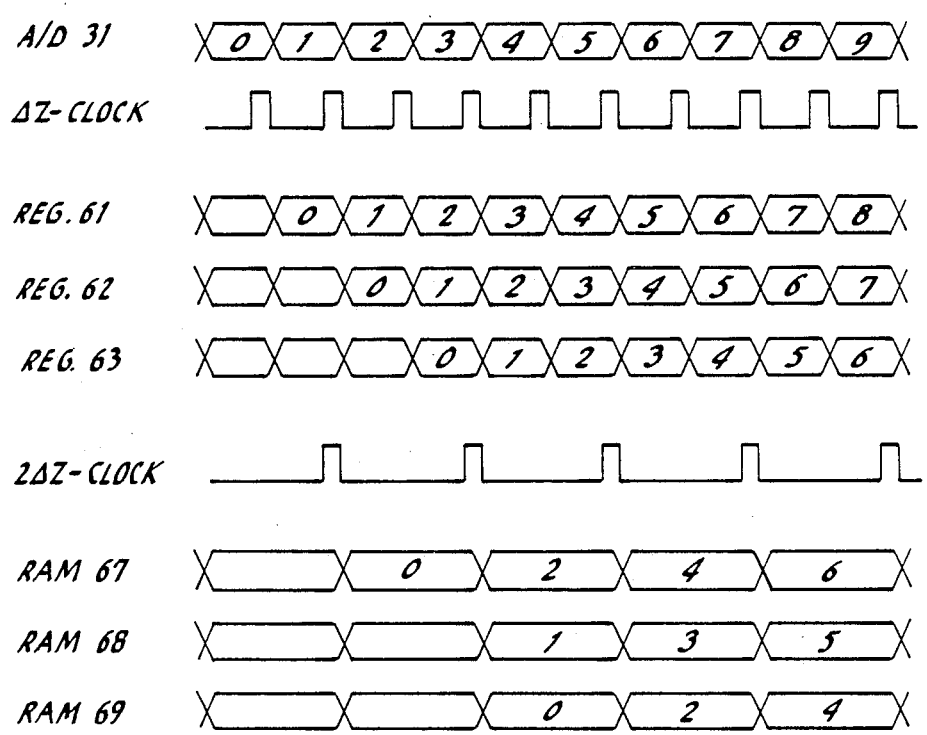
FIG. 9 is a timing diagram associated with the buffer memory of FIG. 8.

FIG. 8 is an illustration of a preferred embodiment of the invention in which details of buffer memory 33 and adder 47 are illustrated. Buffer memory 33 comprises a latch 61 which takes its input from the output of A/D converter 31. The output of latch 61 is applied to the data input of a latch 62 whose output is in turn applied to the data input of a latch 63. The clock inputs of latches 61-63 are connected to timing circuit 32 to supply their respective echo amplitude data at time intervals corresponding to the spatial interval $\Delta Z$. The outputs of latches 61-63 are applied to latches 64, 65 and 66, respectively. Latches 64-66 are clocked at intervals corresponding to a spatial interval $2\Delta Z$ in response to clock pulses supplied on line 36 from timing circuit 32. Successive digital echo samples in latches 61-63 are stored simultaneously into RAMs 67, 68 and 69, so that the most recent one of every three successive echo samples is stored in RAM 67 during a given interval and the same echo sample is stored in RAM 69 as the oldest one of the successive three samples during the next interval, as shown in FIG. 9.

Write address generator 34 is responsive to the 2t-interval clock to write a series of echo samples returning along a given angularly spaced path into respective column locations of a given row of each of the RAMs 67-69. As the transmitted acoustic beam is shifted to the next angular position on the same sector scan field, echoes returning along the next path are stored successively into the next rows of RAMs 67-69.

Buffer memory 33 further includes a first pair of latches 71, 72 and a second pair of latches 73, 74. The output of RAM 67 is connected to the data input of latch 71 and the output of RAM 68 is connected to the data inputs of latches 72 and 73 and the output of RAM 69 is connected to the data input of latch 74. The outputs of latches 71, 72 are respectively connected together with the outputs of latches 73, 74 to input terminals of a reconstructive interpolator 75.

Adder 47 comprises latches 76 and 77 and an 8-bit adder 78. The initial data Zs and the succeeding incremental data $\Delta Z$ are respectively represented by 8 bits for purposes of illustration. These scan conversion data bits are successively supplied on an 8-line bus 79 from ROM 46 to a timing control circuit 80 in response to each tangential increment of the beam transmission path. Timing circuit 80 includes a clock generator which supplies clock pulses at intervals $\Delta Z$ on line 81 to latches 71-74 and 77 and generates a first timing pulse which coexists with the initial data Zs and supplies it on line 82 to the clear terminal of latch 76. Timing circuit 80 further generates a second timing pulse which coexists with the subsequent incremental data ΔZ. The second timing pulse is supplied on line 83 to the input-disabling terminals of latches 76 and 77 to prevent them from responding to the initial bits Zs and incremental bits ΔZ, respectively.

In response to the first timing pulse, latch 76 is cleared and the initial address data Zs is passed through timing circuit 80 to a first input of adder 78 and thence to latch 77 and stored therein. At the end of the first timing pulse, latch 77 is enabled and the initial address data Zs, now stored in latch 77, is supplied to through adder 78 to buffer memory 33.

In response to the second timing pulse, latch 76 is enabled and latch 77 is disabled. The incremental data ΔZ is stored into latch 76 and presented to adder 78. Thereafter, latch 77 is triggered by clock pulses supplied on line 81 to present its contents to adder 78 and causes it to successively add the outputs of latches 76 and 77, thus producing series of incremental address data (Zs+ΔZ), (Zs+2ΔZ), ... (Zs+NΔZ).

The higher four bits of the 8-bit output of adder 78 are applied as a read-address code to RAMs 67, 68, 69, the fifth bit of adder 78 output is applied as a switching signal to latches 71-74 for alternate application of their paired outputs to interpolator 75 and the lower three bits are applied as interpolation address data to the interpolator 75. The effect of interpolator 75 is to compensate for the difference between the amplitude of echo samples derived by A/D converter 31 and the true amplitude of virtual echo samples which would align themselves on both radial and lateral lines in the imge scan field with the virtual echo samples on each radial line being spaced apart by intervals ΔZ/cos θ.

If the initial data Zs is represented by "01000010"(decimal "8.250") and the incremental data ΔZ by "00001001" (decimal "1.125"), the address data generated by the adder 47 will be incremented as shown in FIG. 10. Assume that echo amplitude data at sample points "8" and "9" are stored in latches 71 and 72, respectively, and echo amplitude data at sample points "9" and "10" are stored in latches 73 and 74, respectively. The initial address data Zs (=8.250) is applied to buffer memory 33.

Specifically, address bits "01000" (=8.000) of Zs are applied to RAMs 67-69 and latches 71-74 and interpolation address bits "010" of Zs (=0.250) are applied to supply their contents to interpolator 75. The point of interpolation between sample points "8" and "9" is given by the interpolation address data "010" (=0.250). Interpolator 75 generates a true echo amplitude for the interpolation point 8.250 between sample points "8" and "9" in accordance with the interpolation address data "010" and the pair of echo amplitude data at sample points "8" and "9".

Interpolator 75 is implemented by a microcomputer which operates on the input data in accordance with the following Equation to generate the true echo amplitude Ia:

$$Ia = D_i(1-Ip) + D_{i+1} \cdot Ip \quad (1)$$

where, $D_i$ and $D_{i+1}$ are echo amplitudes at successive sample points, and Ip is interpolation address data. Lookup-table techniques can be advantageously used to process the data at high speeds.

When the address data is incremented to Zs+ΔZ, address bits "01001" (=9.000) are applied to RAMs 67-69 and latches 71-74 and interpolation address bits "011" (=0.375) are applied to interpolator 75. Latches 73 and 74 are enabled to supply amplitude data at sample points "9" and "10" to interpolator 75. Interpolator 75 performs Equation 1 to generate true echo amplitude data for interpolation point "9.375".

A series of reconstructively interpolated echo amplitude data is therefore generated by interpolator 75- in response to the series of incremental address data Zs+nΔZ and supplied at intervals corresponding to ΔZ to graphic memory 38 and stored in cells which are spaced apart at constant intervals ΔX in the row direction and at variable intervals ΔY in the column direction.

Figure 11:
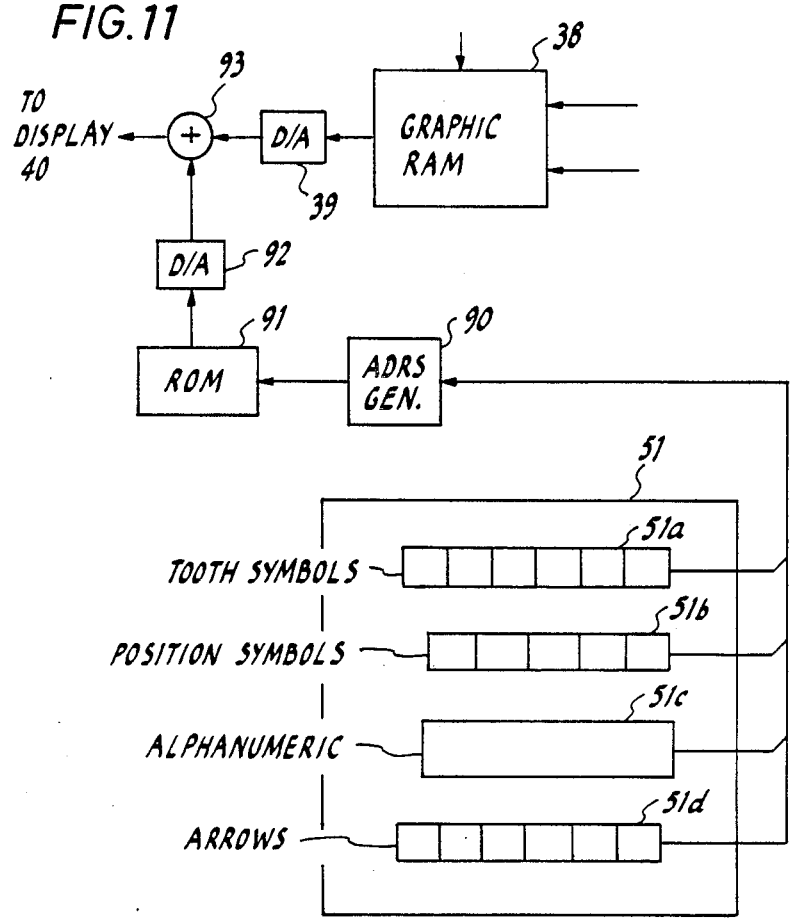
FIG. 11 is an illustration of a modified embodiment which permits visual identification symbols to be selectively displayed on the monitor screen.
Figure 12A:
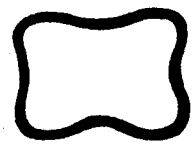
FIGS. 12A to 12G are illustrations of various dental graphic symbols to be displayed on a monitor screen.
Figures 12B, 12C:
Figures 12D, 12E:
Figure 12F:
Figure 12G:
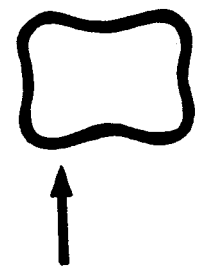

In a practical aspect of the invention, it is preferred to provide visual information by graphic symbols and letters on the monitor 40 to indicate the position and orientation of the probe 1 with respect to the examined object for each of the sector-scanned images displayed on monitor 40. An embodiment shown in FIG. 11 allows visual display of the positional information. Keyboard 51 includes keys 51a-51d which are respectively assigned to specific functions. Keys 51a are assigned to select dental graphic symbols. One of such symbols is shown in FIG. 12A. Keys 51b are used to select position-indicating graphic symbols as shown in FIGS. 12B to 12E which indicate respectively the upper-left, upper-right, lower-left and lower-right portions of the teeth. Alphanumeric keys 51c are assigned to select alphanumeric symbols for display in a position adjacent a dental graphic symbol as shown at FIG. 12F. In combination, the alaphanumeric symbols and position symbols identify the tooth under examination. Keys 51d are used to select arrows indicating the direction in which the probe is oriented with respect to the tooth being examined for display in combination with a tooth symbol as shown in FIG. 12G.

Figure 13:
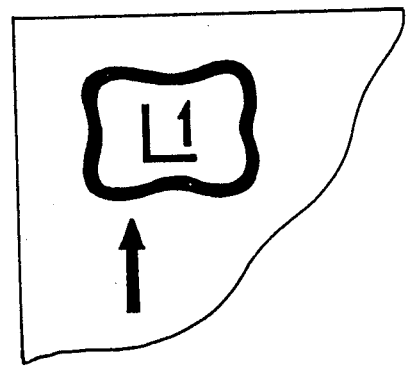
FIG. 13 illustrates a typical combination of dental symbols being displayed on the monitor screen.

The visual information is stored in a ROM 91 which is addressed in response to an address code derived by an address generator 91 from the operated keys. The output of ROM 91 is converted to analog form by a D/A converter 92 and applied to an adder 93 and combined with the output of D/A converter 39 and applied to monitor 40. Desired graphic symbols and alphanumeric symbol are displayed within each of the sector-scan images as shown in FIG. 13.

Figure 14:
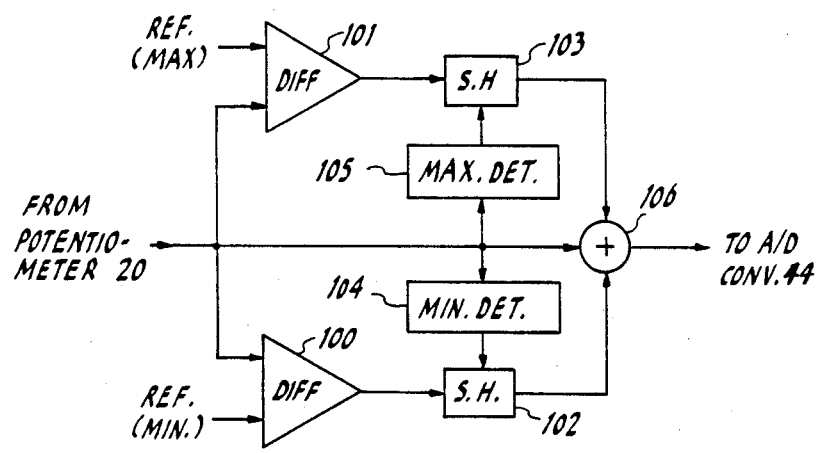
FIG. 14 is a block diagram of a circuit for correcting angular position signals.

FIG. 14 is an illustration of a compensation circuit for compensating for variations of maximum and minimum values of the angular position voltage generated by potentiometer 20 due to mechanical tolerances. The circuit includes a pair of differential amplifiers 101 and 102 each having a first input terminal connected to the output of potentiometer 20. Comparator 100 detects a difference between the potentiometer output voltage and a reference voltage representing a predetermined minimum voltage applied to its second input and supplies its output to a sample-and-hold circuit 102. A minimum detector 104 is connected to potentiometer 20 to detect when the potentiometer voltage drops to a minimum level and supplies a sampling pulse to sample-and-hold circuit 102. This occurs when transducer 4 is angulated to one extreme of its oscillatory motion. The difference between the minimum potentiometer voltage and the predetermined minimum value is registered in the sample-and-hold circuit 102 as a minimum correction voltage and combined with the output of potentiometer 20 in an adder 106 and applied to A/D converter 31.

Likewise, comparator 101 detects a difference between the potentiometer output voltage and a second reference voltage representing a predetermined maximum voltage applied to its seciond input and supplies its output to a sample-and-hold circuit 103. A maximum detector 105 is connected to potentiometer 20 to detect when the potentiometer voltage rises to a maximum level and supplies a sampling pulse to sample-and-hold circuit 103 when the transducer is angulated to the other extreme of its oscillatory motion. The difference between the maximum potentiometer voltage and the predetermined maximum value is registered as a maximum correction voltage in the sample-and-hold circuit 103 and combined with the output of potentiometer 20 in adder 106.

Figure 15:
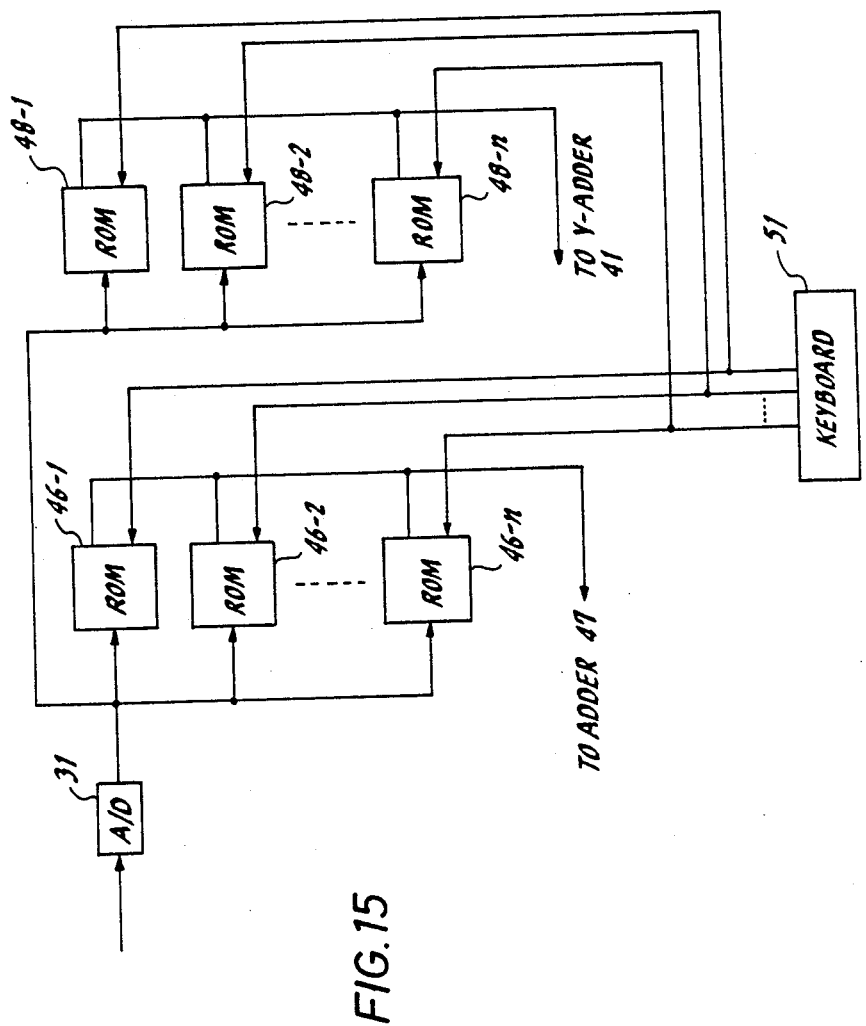
FIG. 15 is a block diagram of a modified embodiment of the invention.

FIG. 15 is a partial depiction of a modified embodiment of the invention. This embodiment includes a plurality of ROMs 46-1 to 46-n and a plurality of ROMs 48-1 to 48-n corresponding to ROMs 46-1 to 46-n. These ROMs are addressed by the otuput of A/D converter 31 and selectively enabled by an enabling signal issued from keyboard 51. Each of these ROMs stores scan conversion data which is specific to a particular type of probe employed in dental diagnosis. Scan conversion data can be changed when different types of probes are interchangeably used.

What is claimed is:

1. An ultrasonic multiple-sector imaging system, comprising:
   an ultrasonic probe having means for generating a beam of acoustic burst energy along each of a plurality of angulated paths with respect to a reference line to provide a sector scan on each of a plurality of angulated planes and for receiving echo signals and a position sensing means for generating a position signal representative of an angular position of each of said paths with respect to said reference line;
   means for sampling said received echo signals at constant time intervals to generate echo samples;
   a buffer memory means for storing said echo samples;
   first read-out means responsive to said position signal for reading echo samples from said buffer memory means at constant time intervals;
   a main memory means having a matrix array of cells arranged in rows and columns;
   area defining means for defining in said main memory means a plurality of storage areas associated respectively with said angulated planes;
   write-in means responsive to said position signal for successively addressing cells of one of said storage areas in synchronism with said first read-out means in directions of the rows and columns so that successively addressed cells are spaced apart in the direction of rows by constant intervals and in the direction of columns by intervals variable as a function of an angle of deflection of each of said paths with respect to said reference line,
   said write-in means further operable for storing echo samples from said buffer memory means into said successively addressed cells so that the stored echo samples describe a sector in each of said defined areas;
   second read-out means for reading echo samples from said main memory means at constant time intervals in the directions of rows and columns; and
   display means for providing display of said echo samples read out of said main memory means in a raster scan field.

2. An ultrasonic multiple-sector imaging system as recited in claim 1, wherein said variable intervals are proportional to the tangent of said angle of deflection.

3. An ultrasonic multiple-sector imaging system as recited in claim 2, wherein said write-in means includes means for generating an address signal representative of the location of each of said cells in said main memory means, and wherein said area defining means comprises:
   X-Y coordinate generating means for generating X- and Y-coordinate signals indicative of X and Y coordinates; and
   comparator means for comparing said address signal with said X- and Y-coordinate signals and for disabling a portion of said main memory means when said address signal exceeds said X- and Y-coordinate signals,
   further comprising a reconstructive interpolator means connected between said buffer memory means and said main memory means for deriving reconstructive interpolated echo samples from successive ones of echo samples read out of said buffer memory means and for applying said derived echo samples to said main memory means as said echo samples stored into said addressed cells, said interpolated echo samples being representative of virtual echo samples on each of said paths, said virtual echo samples being spaced apart in the direction of each of said paths by intervals inversely proportional to the cosine of said angle of deflection, and
   wherein said address signal comprises an initial code representative of a start position of cells in each of said defined storage areas for a series of echo samples derived from each of said paths and a successively incremental code representative of a distance between said start position and each one of the last-mentioned echo samples,
   said interpolator means being responsive to lower significant bits of said incremental code for deriving said interpolated echo samples.

4. An ultrasonic multiple-sector imaging system as recited in claim 2, further comprising a reconstructive interpolator means connected between said buffer memory means and said main memory means for deriving reconstructive interpolated echo samples from successive ones of echo samples read out of said buffer memory means and for applying said derived echo samples to said main memory means as said echo samples stored into said cells, said interpolated echo samples being representative of virtual echo samples on each of said paths, said virtual echo samples being spaced apart in the direction of each of said paths by intervals inversely proportional to the cosine of said angle of deflection.

5. An ultrasonic multiple-sector imaging system as recited in claim 1, wherein said write-in means includes means for generating an address signal representative of the location of each of said cells in said main memory means, and wherein said area defining means comprises:
   X-Y coordinate generating means for generating X- and Y-coordinate signals indicative of X and Y coordinates; and
   comparator means for comparing said address signal with said X- and Y-coordinate signals and for disabling a portion of said main memory means when said address signal exceeds said X- and Y-coordinate signals.

6. An ultrasonic multiple-sector imaging system as recited in claim 5, wherein said address signal comprises an initial code representative of a start position of cells in each of said defined storage areas for a series of echo samples derived from each of said paths and a successively incremental code representative of a distance between said start position and each one of the last-mentioned echo samples.

7. An ultrasonic multiple-sector imaging system as recited in claim 1, wherein said write-in means includes:
   additional memory means for storing a plurality of sets of an initial code representative of a start position of cells in each of said defined storage areas for storing echo samples returning along each of said paths and an interval code representative of an interval between successive ones of the last-mentioned echo samples, each of said sets being stored respectively in locations successively readable out of said additional memory means in response to said angular position signal; and
   adding means for accumulatively adding said interval code to said initial code to generate an incremental address code for addressing said main memory means.

8. An ultrasonic multiple-sector imaging system as recited in claim 1, further comprising:
   means for detecting a maximum value of said position signal and a minimum value of said position signal;
   means for generating a first difference signal representative of a difference between said detected maximum value and a reference maximum value;
   means for generating a second difference signal representative of a difference between said detected minimum value and a reference minimum value; and
   means for correcting said position signal in response to said first and second difference signals.

9. An ultrasonic multiple-sector imaging system as recited in claim 1, further comprising:
   further memory means for storing visual information including shape representative data, position representative data and plane representative data identifying the angulated plane on which said sector scan is provided;
   means for selectively reading the stored visual information out of said further memory means and for combining the read out visual information with information read out of said main memory means.

* * * * *